United States Patent
Martinsen et al.

(10) Patent No.: US 7,856,262 B2
(45) Date of Patent: Dec. 21, 2010

(54) VOLUME SPECIFIC CHARACTERIZATION OF HUMAN SKIN BY ELECTRICAL IMMITANCE

(75) Inventors: Ørjan G. Martinsen, Stabekk (NO); Sverre Grimnes, Oslo (NO)

(73) Assignee: Idex ASA, Fornebu (NO)

( * ) Notice: Subject to any disclaimer, the term of this patent is extended or adjusted under 35 U.S.C. 154(b) by 1506 days.

(21) Appl. No.: 10/513,151

(22) PCT Filed: May 14, 2003

(86) PCT No.: PCT/NO03/00157
§ 371 (c)(1), (2), (4) Date: Aug. 9, 2005

(87) PCT Pub. No.: WO03/094724
PCT Pub. Date: Nov. 20, 2003

(65) Prior Publication Data
US 2007/0043301 A1    Feb. 22, 2007

(30) Foreign Application Priority Data
May 14, 2002    (NO) .................................. 20022310

(51) Int. Cl.
*A61B 5/05* (2006.01)
(52) U.S. Cl. ...................... 600/547; 600/554
(58) Field of Classification Search .............. 600/547, 600/554
See application file for complete search history.

(56) References Cited
U.S. PATENT DOCUMENTS

| | | | |
|---|---|---|---|
| 4,540,002 A | 9/1985 | Atlas | |
| 4,966,158 A | 10/1990 | Honma et al. | |
| 5,738,107 A | 4/1998 | Martinsen et al. | |
| 6,517,482 B1 * | 2/2003 | Elden et al. | 600/309 |
| 2001/0005424 A1 | 6/2001 | Marksteiner | |
| 2003/0176808 A1 | 9/2003 | Masuo | |

FOREIGN PATENT DOCUMENTS

| | | |
|---|---|---|
| JP | 62-27956 A | 2/1987 |
| JP | 10-512764 A | 12/1998 |
| WO | WO 96/10951 A1 | 4/1996 |
| WO | WO 97/14111 A1 | 4/1997 |
| WO | WO 99/23945 A1 | 5/1999 |
| WO | WO 00/19894 A1 | 4/2000 |

OTHER PUBLICATIONS

Martinsen et al., *Facts and Myths about Electrical Measurement of Stratum corneum Hydration State*, Dermatology, 2001, pp. 87-89, vol. 202.

* cited by examiner

*Primary Examiner*—Max Hindenburg
*Assistant Examiner*—Rene Towa
(74) *Attorney, Agent, or Firm*—Rothwell, Figg, Ernst & Manbeck, P.C.

(57) ABSTRACT

This invention relates to a sensor assembly and a method for measuring characteristics of a surface, preferably skin, comprising a first pair of current supply electrodes coupled to a current source, providing an electrical current to the skin, at least one pickup electrodes at chosen positions relative to the current supply electrodes, at least a first of said pickup electrodes being coupled to an instrument for measuring the voltage between said first pickup electrode and at least one of the pickup or current supply electrodes.

6 Claims, 2 Drawing Sheets

VOLUME SPECIFIC CHARACTERIZATION OF HUMAN SKIN BY ELECTRICAL IMMITANCE

CROSS REFERENCE TO RELATED APPLICATION

This application is a 35 U.S.C. §371 National Phase Entry Application from PCT/N003-00157, filed May 14, 2003, and designating the U.S.

This invention relates to a sensor assembly and a method for measuring characteristics of a surface, preferably skin, and more specifically a system for volume specific immittance measurements on human skin. The measurements are done in order to characterize the physiological conditions of the specific skin volume, like e.g. viability, moisture content, structure, composition, etc. Examples of possible applications for this invention are for life detection in fingerprint recognition systems, depth specific skin hydration measurements or detection of electrodermal response localized to discrete sweat duct orifices.

Measurement depth for bioimpedance measurements on skin will in general greatly depend on the frequency of the applied signal—higher frequency will mean measurements at a greater depth in the skin, as is discussed in Martinsen Ø.G., Grimes S., Haug E.: Measuring depth depends on frequency in electrical skin impedance measurements. Skin Res. Technol., 5, 179-181, 1999. Impedance spectroscopy on a well-defined skin volume is hence impossible with conventional techniques, since each frequency will represent a different volume of the skin. However, the invention described here enables a higher degree of focused multi-frequency measurements on specific skin layers or volumes.

Measuring of tissue characteristics using electrodes are known from a number of other publications as well, such as U.S. Pat. No. 6,175,641, which does not take into account the layered nature of the skin, U.S. Pat. No. 5,353,802, which is aimed at in depth interrogation of organs using concentric ring electrodes and U.S. Pat. No. 5,738,107, which measures the moisture content of the skin by the use of relatively large electrodes. None of these have the possibility to selectively measure the specific skin layers being the object of this invention.

Another known solution for measuring skin characteristics are described in international patent application No PCT/AU98/00925 wherein a solution is discussed for detecting abnormalities in the skin. The local impedance around a small electrode is used to measure the degree of damage made to the skin, and thus indirectly also the depth of the damage. The described method does not provide possibilities to measure map the characteristics of the skin layers through the impedance measurements, e.g. being necessary for confirming if a finger is constituted by living tissue.

Measurements of skin layers is discussed in U.S. Pat. No. 4,540,002 wherein the four electrodes are used, two electrodes for applying a constant current to the skin and two for measuring the impedance in the skin. Thus the impedance between the current application electrodes are removed from the measurements. In reality this system is impractical and does not take into account the complex part of the impedance signal.

U.S. Pat. No. 4,966,158 described moisture measurement in skin, and does not allow for in depth measurements of the different skin layers, while US application No 2001/0005424 A1 describes a very simple way to use two electrodes for measuring skin impedance for live finger detection purposes in practice the latter will not give sufficient reliability because it is easy to make false fingers having the same impedance characteristics as required in the application.

Thus it is an object of this invention to provide a method and sensor assembly for measuring characteristics of a surface giving reliable in depth measurements of tissue close to a surface e.g. for live finger confirmations and skin hydration measurements.

The object of this invention is obtained as is described in the independent claims.

The invention will be described below with reference to the accompanying drawings, which described a preferred embodiment of the invention by way of example.

Figure 1:
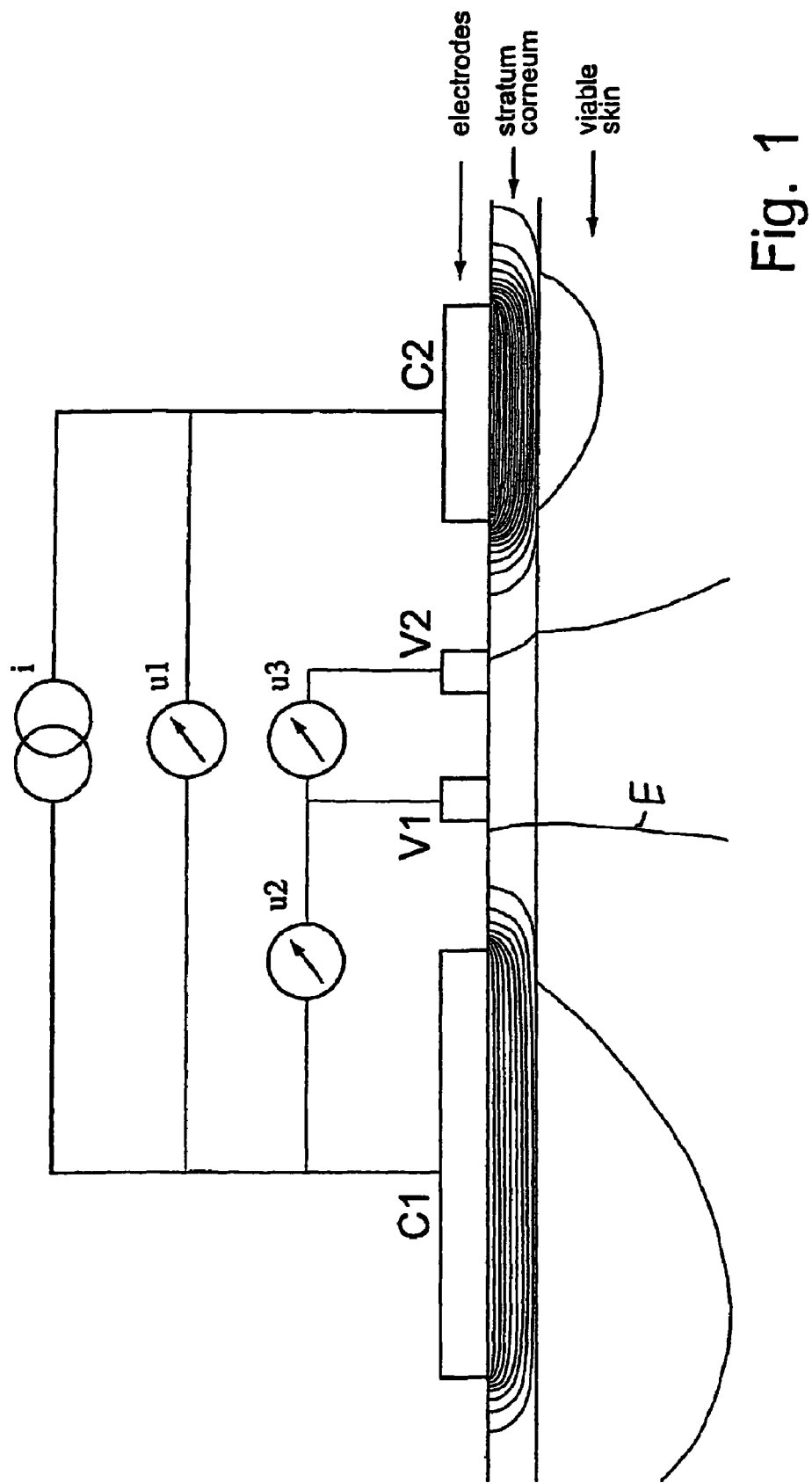
FIG. 1 illustrates an assembly according to the invention.

Measurements using electrodes with a size comparable to the thickness of the stratum corneum (SC) will, because of the high current density in the vicinity of the electrodes, focus the measurements on the SC alone. This is illustrated in FIG. 1 where a finite element (FEM) simulation has been performed at 100 kHz on a system comprising four metal electrodes (C1, C2, V1 and V2) on top of a layer of epidermal SC, again on top of a layer of viable skin. (FIG. 1 shows only a segment of the total simulated model.) The electrodes may be galvanically coupled to the skin surface or the voltage may be coupled to the skin through a dielectricum or air.

FIG. 1 shows equipotential lines E and thus clearly illustrates that any monopolar measurement on electrodes C1 or C2, or a bipolar measurement u1 between these two electrodes, will be totally dominated by the SC.

Furthermore, utilising a voltage pick-up electrode (V1 or V2) adjacent to the current-carrying electrode will make it possible to focus the measurements on the SC also for larger electrodes. Although the equipotential lines will change as a function of e.g. SC hydration and other variables, simulations where the admittivity of the SC was varied over an extreme range of six orders of magnitude (values from $10^{-3}$ to $10^{+3}$ times the normal values for stratum corneum were choosen) showed e.g. that a voltage pick-up electrode situated about 1-2 times the thickness of the SC from the current-carrying electrode would always hit an equipotential line delimiting a volume comprising most of the SC thickness and no significant contribution from viable skin.

Hence measuring the differential voltage u2 between this electrode and the current carrying electrode will always yield isolated measurements on SC, whereas voltage measurements u3 between the first pickup electrode electrode and the next voltage pick-up electrode (V1 and V2 in FIG. 1) will always give results that are totally dominated by viable skin (always using C1 and C2 for current injection). Since the SC is much less conductive (or more correct; admittive), the parts of the measured volume extending into the SC in the latter, tetrapolar measurement will have very low current density and hence contribute only insignificantly to the measured values. The pickup electrodes in this setup should be small and should not be positioned too close to the current supply electrodes C1 or C2, in order to avoid any electrical current going via the pickup electrodes V1 or V2.

The invention described here is based on using one or more voltage pick-up electrodes in combination with current-injecting electrodes to enable characterisation of well-defined skin volumes by measuring their electrical immittance. One or more volumes may be measured and these volumes may be measured simultaneously or in sequence. By alternating the relationship between the electrodes, e.g. by measuring voltage between the pickup electrodes and between each pickup electrode and each supply electrode, different depths may be measured and thus a characterisation of the skin layers may be obtained.

Furthermore the preferred size of the pickup electrodes, being comparable to the thickness of the SC, or 0.01 mm to 0.5 mm depending on the skin on the chosen part of the body, allows for detection of small features and the use of relatively high frequencies. When measuring the characteristic of SC the distance between the pickup electrode and the closest current supply electrode between which the voltage is measured, is in the same range, i.e. the thickness of the SC or less than 1 mm.

Based on the voltage or impedance measurements performed by the pick-up electrodes the characteristics of a finger surface may thus be measured to a certain depth, depending the electrode distance and configuration. The four-electrode embodiment comprising two pickup electrodes will represent only deeper, living skin layers if the distance between the current and voltage electrodes are larger than the SC thickness (e.g. approximately 50-100 µm from the surface). If the distance is smaller the lateral conductivity in the SC will contribute and a tissue characteristics such as anisotropies in the SC.

EXAMPLE 1

Live Finger Detection

In any electronic system for fingerprint recognition, it will always be important to be able to detect the presence of a dummy finger or a dead (cut-off) finger. While a dummy finger made of a material like e.g. rubber would be rather easy to detect with any one of several different techniques, a thin layer of pattern-imprinted latex covering a real, living finger would be a greater challenge. Such a finger would share most characteristics with a genuine finger, like e.g. temperature, blood pulse, etc. Any conventional electrical immittance measurement (like e.g. the one described in U.S. Pat. No. 6,175,641) will also easily fail if the user e.g. applies some moisture (e.g. saliva) on the latex surface.

In the case of a dead (cut-off) finger, the most obvious differences to a living finger are that a living finger presumably is warmer than a dead one, that a living finger will have blood pulse and that this blood will be oxygenated. Research has furthermore shown that the electrical properties of living tissue are dramatically changed post mortem. A large number of research papers have been published on post mortem changes in the electrical properties of tissue e.g. from muscle, liver, lung and brain. One example from our own group is: Martinsen Ø.G., Grimnes S., Mirtaheri P.: Non-invasive measurements of post mortem changes in dielectric properties of haddock muscle—a pilot study. J. Food Eng., 43(3), 189-192, 2000.

A thermal detection of life will fail because of the obvious procedure of just heating e.g. a cut-off finger inside your hand. Infrared assessment of blood oxygen is another possibility, but will not work e.g. in cold weather since the body will turn off microcirculation in the fingers when ambient temperature drops. Pulse measurements based e.g. on impedance plethysmography will be extremely difficult to carry out in practice since the dynamic signal even in an optimized system is typically only 0.1%, and furthermore that these measurements will share the same problems in cold weather. Pulse measurements based on ECG signals-could of course be an alternative, but one finger alone would not pick up any signal, which makes even this approach uninteresting.

The invention described here will make it possible to measure the immittance of the SC and viable skin layers simultaneously, at one frequency or a range of frequencies, preferably in the range of 10-1000 kHz, especially approximately 100 kHz. The complex components can be measured using synchronous rectifiers or the Kramers-Kronig relations can be utilised in order e.g. to deduce the phase response from the modulus. Characteristics like e.g. electrical anisotropy may also be used in a multivariate model to improve this live finger detection method.

Figure 2:
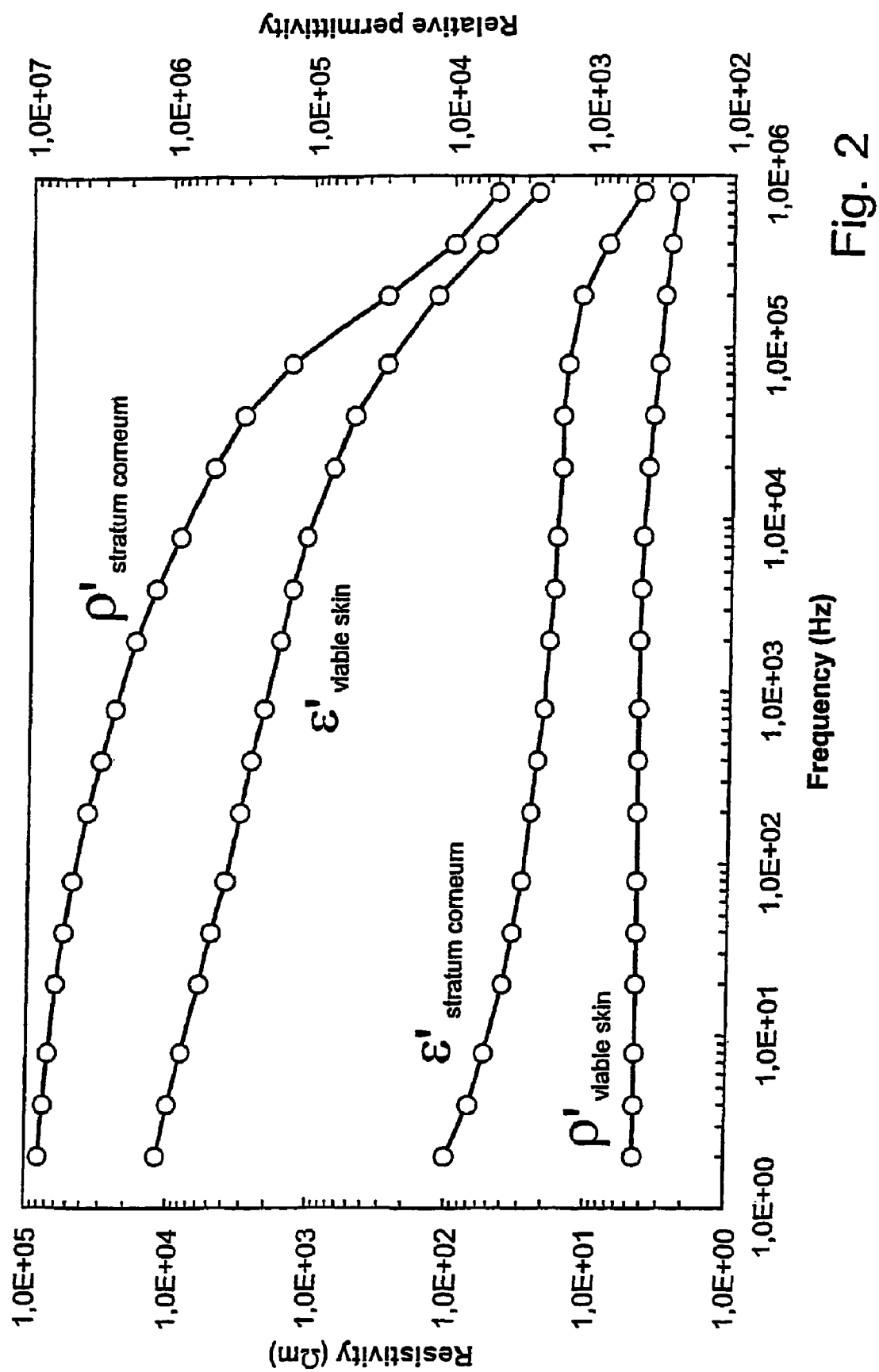
FIG. 2 illustrates the resistivity and relative permittivity for stratum corneum and viable skin.

FIG. 2, being a citation from Yamamoto and Y. Yamamoto, Med. Biol. Eng. Comput., 14, 592-594, 1976, shows that stratum corneum and viable skin has very different electrical properties, especially at low frequencies but also e.g. at 100 kHz where the difference in resistivity is about 400 times and in relative permittivity about 20 times. In addition, the frequency response is very different for stratum corneum and viable skin. The stratum corneum has a significant dispersion in the resistivity whereas the resistivity of the viable skin is rather constant, and the other way around for the permittivity. A system for live finger detection where focused measurements on both these skin layers are done simultaneously, will be difficult to fool, both because of the characteristic and very different electrical properties of these two layers, and because the properties of the viable skin changes dramatically post mortem. In the case of a genuine finger with a thin latex layer, this three-layered structure can easily be detected and the system cannot longer simply be fooled by setting up an electric current in a moisture layer on the surface.

EXAMPLE 2

Skin Hydration Measurements

Skin function is extremely dependent on the hydration state of the epidermal SC. By monitoring the hydration state of the stratum corneum, an early diagnosis of non-visible skin conditions may be accomplished. In addition, measurement of SC hydration is also important in the evaluation of the effects of topical formulations like e.g. skin moisturisers.

We have earlier developed an electrical method for skin hydration measurements, based on low frequency susceptance measurements (see e.g. U.S. Pat. No. 5,738,107). There is reason to believe that multi-frequency measurements on SC will provide additional information that may be useful in the assessment of SC hydration and condition, but the fact that multi-frequency measurements on pure SC in vivo has been impossible to accomplish until now, has prevented further investigation in this area.

The invention described here will thus enable focused multi-frequency measurements on selected skin layers like e.g. the SC. With careful selection of electrode size and geometry, it will also be possible to achieve measurements within different layers in the SC itself. This will be important since we already know that the water is not homogenously distributed in the SC, but rather appears as a water gradient with the innermost layers in balance with the moist, viable layers and the outer layers in balance with the ambient relative humidity.

EXAMPLE 3

Localized Measurement of Exogenic Electrodermal Response

The sweat activity on palmar and plantar skin sites is very sensitive to psychological stimuli or conditions. The changes are easily detected by means of electrical measurements and since the sweat ducts are predominantly resistive, a low frequency or dc conductance measurement is typically used in electrodermal response (EDR) measurements.

The lie detector is perhaps the most commonly recognized instrument where the electrical detection of EDR activity is utilized. There are, however, several other applications for such measurements, mainly within the two categories; neurological diseases or psychophysiological measurements. Examples of the first category are neuropathies (e.g. diabetes), nerve lesions, depressions and anxiety. The latter category may include emotional disorders, pain assessment and lie-detection.

EDR measurements are conventionally performed with skin electrodes that are much larger than the area typically occupied by one single sweat duct orifice. Hence, only the overall or mean effect of many individual sweat ducts is measured. Since the innervation of the sweat glands not necessarily is synchronous, there is potentially more information available if one could focus the measurements on a smaller area.

The invention described here will enable such measurements on a small, well defined volume of the skin and will hence be valuable in future generations of instruments for EDR measurements.

The method according to the invention thus may be summarized as method for measuring the electrical characteristics of two outer parts of the skin, i.e. the stratum corneum and the viable skin, comprising the steps of applying a current or voltage to the skin between two supply electrodes, measuring the voltage between one of said supply electrodes and a first electrode positioned at a chosen distance from said supply electrode, measuring the voltage between the first and a second electrode, the second electrode being positioned at a larger distance from the first supply electrode than the first electrode, and comparing the voltages measured at the two electrodes for providing the permittivity and/or resistivity of at least one of the skin layers. The role of the two pickup electrodes may shift so as to allow for measuring of different depths. This, however, requires that the distances between the electrodes are unequal.

For measurement close to the surface it may be sufficient to measure the voltage between one of said supply electrodes and only one pickup electrode positioned at a chosen distance from said current supply electrode. Then, however, the distance should be comparable to the thickness of the SC in order to obtain measurements of the surface area.

The invention claimed is:

1. Method for inspecting whether an object consists of living skin, the method comprising the following steps:

measuring electrical characteristics of two outer layers of skin, wherein said two outer layers of skin comprise respectively a stratum corneum and living skin, comparing the measured electrical characteristics with corresponding, known characteristics of skin of a living or a dead finger, wherein the measurements of electrical characteristics in the two skin layers is characterized in applying an alternating current or voltage with at least one frequency to the skin between two current supply electrodes, measuring a complex voltage as a function of frequency between one of said current supply electrodes and a first electrode positioned at a chosen distance from said one current supply electrode for said at least one frequency, measuring a complex voltage between the first electrode and a second electrode, wherein the second electrode is positioned at a larger distance from said one first current supply electrode than said first electrode for said at least one frequency, calculating immittance for the two skin layers based on said voltage measurements, and using said immittance as a basis for comparing with corresponding, known characteristics of skin of a live or a dead finger.

2. Method according to claim 1, wherein said comparison of electrical characteristics comprises comparing dispersion of resistivity for at least one skin layer.

3. Method according to claim 1, wherein said comparing of electrical characteristics comprises comparing dispersion of permittivity for at least one skin layer.

4. Method according to claim 1, wherein said comparing of electrical characteristics comprises comparing resistivity for at least one skin layer.

5. Method according to claim 1, wherein said comparing of electrical characteristics comprises comparing relative permittivity for at least one skin layer.

6. Method according to claim 1 wherein the distance between said one current supply electrode and said first electrode is less than 1 mm.

* * * * *